(12) United States Patent
Bittner

(10) Patent No.: US 11,357,577 B2
(45) Date of Patent: Jun. 14, 2022

(54) DETERMINING A SUITABLE ANGULATION AND DEVICE

(71) Applicant: Siemens Healthcare GmbH, Erlangen (DE)

(72) Inventor: Maik Bittner, Langensendelbach (DE)

(73) Assignee: Siemens Healthcare GmbH, Erlangen (DE)

(*) Notice: Subject to any disclaimer, the term of this patent is extended or adjusted under 35 U.S.C. 154(b) by 420 days.

(21) Appl. No.: 16/503,621

(22) Filed: Jul. 4, 2019

(65) Prior Publication Data

US 2020/0008885 A1 Jan. 9, 2020

(30) Foreign Application Priority Data

Jul. 4, 2018 (EP) .................... 18181684

(51) Int. Cl.
*A61B 6/00* (2006.01)
*A61B 34/20* (2016.01)
*A61B 34/10* (2016.01)
*A61M 25/09* (2006.01)

(52) U.S. Cl.
CPC .............. *A61B 34/20* (2016.02); *A61B 6/461* (2013.01); *A61B 6/5205* (2013.01); *A61B 34/10* (2016.02); *A61M 25/09* (2013.01); *A61B 2034/107* (2016.02)

(58) Field of Classification Search
CPC ... A61B 2034/107; A61B 34/10; A61B 34/20; A61B 6/12; A61B 6/461; A61B 6/481; A61B 6/487; A61B 6/504; A61B 6/5205; A61B 6/54; A61M 25/09
See application file for complete search history.

(56) References Cited

U.S. PATENT DOCUMENTS

| | | |
|---|---|---|
| 2011/0196395 A1 | 8/2011 | Maschke |
| 2012/0250964 A1 | 10/2012 | Pfister |
| 2014/0294149 A1 | 10/2014 | Rieber et al. |
| 2019/0346319 A1 | 11/2019 | Bydlon et al. |

FOREIGN PATENT DOCUMENTS

| | | |
|---|---|---|
| CN | 104068877 A | 10/2014 |
| DE | 102010007177 A1 | 8/2011 |
| DE | 102010022526 A1 | 10/2011 |
| DE | 102011006484 A1 | 10/2012 |
| WO | 2018104162 A1 | 6/2018 |

OTHER PUBLICATIONS

European Search Report for European Patent Application No. 18181684.4-1124 dated Jan. 24, 2019.

*Primary Examiner* — Mark D Remaly
(74) *Attorney, Agent, or Firm* — Lempia Summerfield Katz LLC

(57) ABSTRACT

A method is provided for automatically determining a suitable angulation or inclination of a recording system during a navigation of a guide wire through a vascular system of a patient from a vessel into a branch of the vessel. The method includes recording a sequence of live X-ray images of the guide wire and presenting the X-ray images on a display unit. A first virtual tangent is applied to a first section of the guide wire, and a second virtual tangent is applied to a second section of the guide wire on the X-ray images. A point of intersection of the virtual tangents is determined on the X-ray images, and a triangle is determined. An area of the triangle is determined, and the suitable angulation or inclination of the recording system is determined by maximizing the area of the triangle by movement of the recording system.

9 Claims, 2 Drawing Sheets

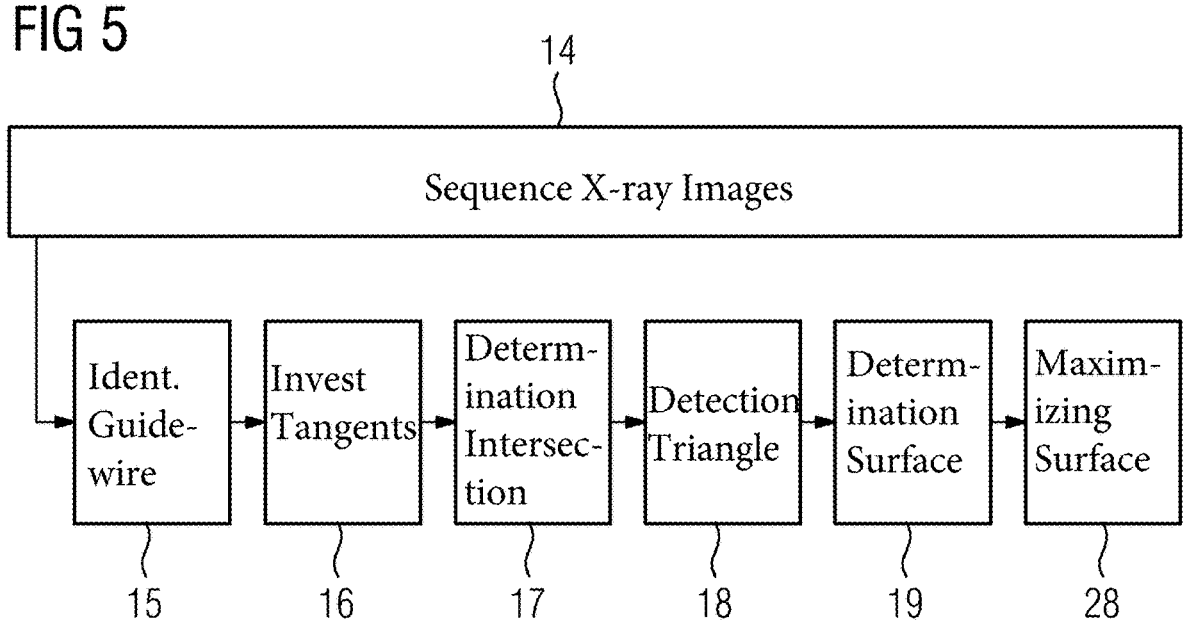
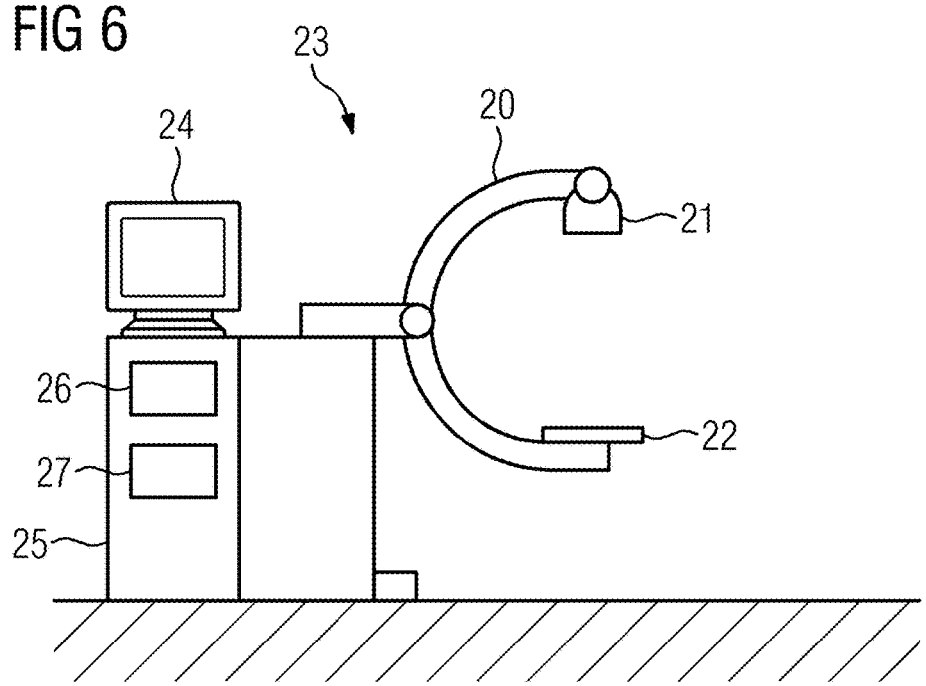

DETERMINING A SUITABLE ANGULATION AND DEVICE

This application claims the benefit of European Patent Application No. 18181684.4, filed on Jul. 4, 2018, which is hereby incorporated by reference in its entirety.

BACKGROUND

The present embodiments relate to determining a suitable angulation of a recording system for a visualization of a guide wire.

When performing certain endovascular interventions, a guide wire is to be navigated through blood vessels from, for example, a vessel 1 into a branch of the vessel (e.g., into a side branch 2 of the vessel) (see FIG. 1). This is generally performed using real-time monitoring using a fluoroscopic X-ray device (e.g., a C-arm device). The guide wire 4 is directed by a tip 5, where by turning the whole guide wire system in the direction of rotation 6, the tip 5 is oriented in the direction of the target vessel and then introduced (see FIG. 2).

In general, two views are necessary in order to perform the procedure: (P1) is the side view of the outflow of the vessel 1 into the side branch 2; as the outflow may be shown as a virtual ring 3, in the side view (P1) this becomes a line, and (P2) is the view of the plane that the curved guide wire virtually spans through the curvature so that the curvature may be seen to the maximum. To determine these views, the recording system of the fluoroscopy device, in general a C-arm, is to be rotated accordingly while administering contrast agent until the views seem suitable to the user. As endovascular examinations and/or interventions are mainly used for multi-morbid and/or very elderly patients for whom an open surgical operation would pose too great a risk, an intervention with the shortest duration possible and the use of as little contrast agent as possible is desirable. If no curvature of the guide wire is visible in the X-ray image, then the angulation of the C-arm is such that, in terms of a central beam, views the curvature from "behind". The curvature may be seen to the maximum when the central beam of the C-arm forms a perpendicular to the plane of the curvature of the guide wire (P2).

Automatic methods already exist to determine the side view (P1). Thus, the outflow of the vessel into the branch is first shown as a virtual ring in the fluoroscopy X-ray image, and the recording system is then moved so that the virtual ring in the representation becomes a straight line (syngo EVAR Guidance™ and syngo Aortic Valve Guidancen™). To determine the view (P2), the user is to move the C-arm manually and/or semi-automatically until in a view, the curvature is visible to the maximum.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method that quickly enables suitable views of a curved guide wire from a vessel of a patient into a branch of the vessel is provided. As another example, an X-ray device suitable for carrying out the method is provided.

The method according to an embodiment for automatically determining a suitable angulation of a recording system for a visualization of a guide wire during a navigation of the guide wire through a vascular system of a patient from a vessel into a branch of the vessel is provided. The guide wire has a curvature and a first proximal section on the first side of the curvature and a second distal section having the tip of the guide wire on the second side of the curvature. The method includes recording a sequence of live X-ray images (e.g., a rapid sequence of live X-ray images) of the guide wire and presenting the X-ray images on a display unit. At the same time, the guide wire is identified (e.g., by an image recognition algorithm) in the X-ray images. A first virtual tangent is applied to the first section, and a second virtual tangent is applied to the second section of the guide wire on the X-ray images. A point of intersection of the virtual tangents is determined on the X-ray images, and a triangle is determined. Three corners of the triangle are the point of intersection, and a first point on the first section and a second point on the second section on the X-ray images. The area of the triangle is determined, and the suitable angulation of the recording system is determined by maximizing the area of the triangle by movement of the recording system.

Using one or more of the present embodiments, an optimum angulation of the recording system may be automatically achieved with regard to the curved guide wire such that the central beam of the recording system forms a perpendicular to the plane spanned by the curvature, and in doing so, an optimum view to present the navigation of the guide wire from a vessel of the patient into a branch of the vessel. For this purpose, the area of the virtual triangle, the sides of which form the virtual tangents, is maximized, and/or the recording system is automatically moved until the area of the triangle reaches a maximum.

The first point on the first section may be freely selected automatically or beforehand manually but is to, as soon as selected, then remain the same point throughout the method. According to an embodiment, the first point is formed by the point of contact of the first tangent with the first section and the second point by the point of contact of the second tangent with the second section. The point of contact may be the point at which the tangent first comes into contact with the respective section. According to a further embodiment, the second point is formed by the tip of the guide wire.

The optimum angulation may be found very quickly by the method so that the navigation of the guide wire may be performed quickly and thus sparingly for the patient. The duration of the X-ray radiation and duration of the administration of a contrast agent of the patient may be reduced by the method so that the patient suffers less discomfort as a result of the method than as a result of methods of the prior art.

In the simplest case, the triangle is right-angled and/or isosceles.

According to an embodiment, the suitable angulation of the recording system is determined by first positioning (a) the recording system such that the central beam forms a perpendicular on the first section and (b) the recording system is then rotated around the first section and/or the first tangent as an axis of rotation in order to maximize the area of the triangle. The first section of the guide wire is therefore first optimally visualized so that the final alignment of the recording system may only be performed by rotating the recording system. Act (a) with regard to the first section and/or the first tangent may be performed simply and quickly as generally speaking, the corresponding vessel and/or the guide wire is already sufficiently well shown by X-ray images. Overall, this results in the very fast and simple discovery of suitable angulation.

Alternatively, the suitable angulation of the recording system may also be determined by (a) first positioning the recording system such that the central beam forms a perpendicular on the second section and (b) thereafter, the recording system is rotated around the second section and/or the second tangent as the axis of rotation to maximize the area of the triangle.

According to a third alternative, the suitable angulation of the recording system may also be determined by movement of the recording system in an orbital motion to maximize the area of the triangle. In this case, the presentation of the first section and the second section are optimized at the same time, and the recording system is moved in several degrees of freedom during the maximization of the virtual triangle.

According to a further embodiment, the corresponding pixels on the X-ray images are automatically counted to determine the area of the triangle. Alternatively, the length of the sides of the triangle may also be used for calculation.

According to a further embodiment, the suitable angulation thus determined is then automatically selected to visualize the navigation of the guide wire through a vascular system of a patient from a vessel into a branch of the vessel. In this way, the practitioner may perform the intervention quickly and with optimum visual monitoring.

One or more of the present embodiments also include a medical X-ray device for carrying out the method. The medical X-ray device includes a recording system that may be moved in a multiplicity of angulations with regard to a patient. The recording system includes an X-ray source and an X-ray detector for recording X-ray images of the patient. The medical X-ray device includes a control unit for controlling the X-ray device, a display unit for displaying the recorded X-ray images, an image processing unit for processing the X-ray images, and a calculation unit.

BRIEF DESCRIPTION OF THE DRAWINGS

FIG. 5 shows a sequence of acts of one embodiment of a method; and

FIG. 6 shows an X-ray device according to an embodiment for carrying out the method.

DETAILED DESCRIPTION

Figure 1:
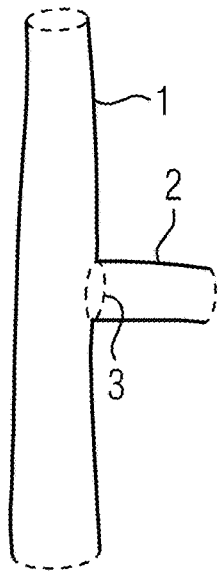
FIG. 1 shows a side view of a vessel of a patient and a branch of the vessel.
Figure 2:
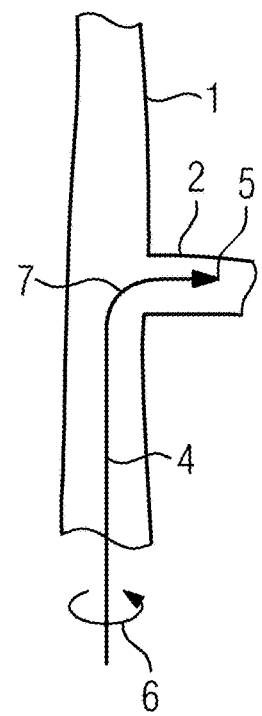
FIG. 2 shows a side view of a vessel and a branch with a guide wire.

FIGS. 1 and 2 show a vessel 1 of a patient and a side branch 2 of the vessel into which a guide wire 4 is to be introduced. The guide wire has a curvature 7 that is achieved by navigating into the side branch 2. This often occurs in the context of endovascular interventions, and for monitoring purposes, a sequence of live X-ray images is recorded by medical fluoroscopic X-ray devices. To perform the procedure, in general, two views are necessary: (P1) is the side view of the outflow of the vessel 1 into the side branch 2; as the outflow may be shown as a virtual ring 3, in the side view (P1), it becomes a line, and (P2) is the view on the plane that virtually spans the curved guide wire through the curvature so that the curvature is visible to the maximum.

The method according to one or more of the present embodiments automatically determines a suitable angulation and/or inclination of the C-arm for (P2) quickly and particularly precisely. FIG. 5 shows a sequence of acts of the method according to one or more of the present embodiments. In a first act 14, a sequence of live X-ray images (e.g., fluoroscopic X-ray images) of the guide wire is recorded and shown on a display unit. The following acts two to eight are carried out during the first acts (e.g., during real-time monitoring by X-ray images).

Figure 3:
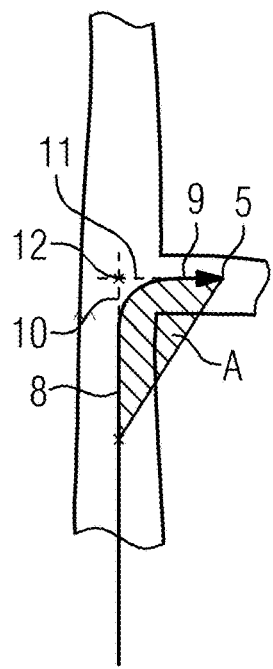
FIG. 3 shows a view of a guide wire with triangular area.
Figure 4:
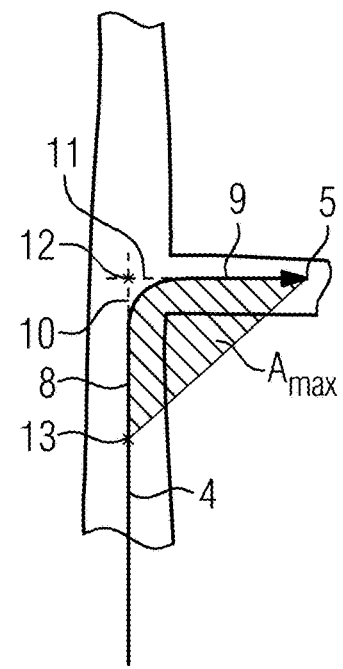
FIG. 4 shows a suitable view of a guide wire with maximum triangular area.

In a second act 15, the guide wire is identified on at least some of the X-ray images. This may be performed, for example, by an image recognition algorithm. Provided that the guide wire and the recording system do not move, it may be assumed that the guide wire on the X-ray images remains at the same place. The identified guide wire may also be superimposed/marked on the X-ray images to make the following acts easier. In FIGS. 3 and 4, the guide wire 4 with a first proximal section is on the first side of the curvature, and a second distal section 9 having the tip 5 of the guide wire is on the second side of the curvature.

In a third act 16, a first virtual tangent 10 is subsequently applied to the first section, and a second virtual tangent 11 is applied to the second section of the guide wire. In a fourth act 17, the point of intersection 12 of the first tangent 10 and the second tangent 11 determined. These two acts may also, for example, be performed by software and/or an image processing unit.

In a fifth act 18, a triangle is determined. Three corners of the triangle are the point of intersection and a first point 13 on the first section and a second point on the second section. The first point on the first section and the second point on the second section may be (e.g., automatically or manually) selected at random, but are to remain the same in the subsequent act. For easy selection, the point of contact of the first tangent with the first section (e.g., internal) may be used as the first point and the point of contact of the second tangent with the second section (e.g., internal) may be used as the second point. Alternatively, for example, the tip of the guide wire may be used as the second point. In a sixth act, the area A of the virtual triangle is determined. For example, the corresponding points and the area of the triangle may be determined by software. If the triangle is right-angled, then an area of the triangle is simply $A=ab/2$, where a and b are the sides of the triangle. If the triangle is not right-angled, the pixels may be counted to determine the area.

Subsequently, in a seventh act 28, the area of the triangle is maximized while moving the recording system. In the process, the recording system is moved automatically (e.g., rotated) until the area of the triangle has reached a maximum. Once the maximum has been reached, it may be assumed that the central beam of the recording system forms a perpendicular on the plane of the curvature of the guide wire and in doing so, the curvature is visible to the maximum. The angulation and/or inclination of the C-arm at which the maximum is reached is therefore ideally suited for the visualization of the curvature.

The movement of the recording system may be started automatically or triggered by an input. There are several suitable options for moving the recording system to find the maximum of the triangular area, each based on the initial angulation or inclination of the recording system. If this is arbitrary, the recording system may be moved in an orbital motion.

Alternatively, the recording system may first be positioned in such a way (or has already been positioned in such a way previously) that the central beam forms a perpendicular on the first section. Then, the recording system is rotated around the first section to maximize the area of the triangle.

As a third alternative, the recording system may first be positioned in such a way (or is already positioned in such a way) that the central beam forms a perpendicular on the second section. Then, the recording system is rotated around the second section to maximize the area of the triangle.

Once the angulation or inclination of the C-arm at which the triangular area has a maximum is found, the recording system may then be automatically moved into this angulation or inclination and/or remain there so that the interventional procedure may be continued. If, for example, the position of the guide wire is changed, the method may be repeated to find and select a new optimally suitable angulation or inclination. The method may be carried out such that no user intervention is necessary. If necessary, a user input may also be requested, for example, to select the points or to continue the method.

FIG. 6 shows a medical X-ray device 23 according to one or more of the present embodiments. This has, for example, a C-arm 20 with an X-ray source 21 and an X-ray detector 22 as a recording system. The medical X-ray device 23 is controlled by a control unit 25 and has a display unit 24 to display X-ray images. An image processing unit 26 and a calculation unit 27 that, for example, may carry out the corresponding acts of the method by software are present.

A virtual tangent is applied to the first section and the second section, respectively, to solve the problem (p2). The second section may exhibit the tip of the guide wire. The tangents intersect above the curvature of the guide wire. If the point of intersection is connected to the points of contact of the two sections, this creates a triangle. The imaging system tracks the guide wire by fluoroscopy. Software may detect and determine the corresponding points and the area of the triangle. If the triangle is right-angled, then an area is where a and b are the sides of the triangle. If the triangle is not right-angled, the pixels may be counted, for example, to determine the area. The recording system moves automatically or is triggered by an input until the area of the triangle is maximized. Using one or more of the present embodiments, an optimum top view of the recording system may automatically be achieved on the plane spanned by the curved guide wire such that the central beam of the recording system forms a perpendicular on the plane. This is achieved by determining the angulation and/or inclination of the C-arm at which the triangle spanned by the guide wire is at a maximum. Compared to a manual setting of such a top view, this may be achieved more precisely and quickly. This is helpful in time-sensitive and acute situations in the operating theatre. In addition, doses may be saved, and the patient is thus subjected to less discomfort. A manual setting costs more time and is less precise and more complicated.

The use of markers in the tip 5 of the guide wire, on the curvature, and on the first section of the guide wire may optimize the method (e.g., with regard to image recognition algorithms and calculation of the triangular area), but the method also functions with all other guide wires.

One or more of the present embodiments may be briefly summarized as follows: To improve patient safety during interventional procedures with guide wires, a method is provided for automatically determining a suitable angulation or inclination of a recording system during a navigation of the guide wire through a vascular system of a patient from a vessel into a branch of the vessel for a visualization of a guide wire. The guide wire has a curvature and a first proximal section on the first side of the curvature and a second distal section having the tip of the guide wire on the second side of the curvature. The method includes recording a sequence of live X-ray images of the guide wire and presenting the X-ray images on a display unit. At the same time, the method includes identifying the guide wire on the X-ray images, and applying a first virtual tangent to the first section and a second virtual tangent to the second section of the guide wire on the X-ray images. A point of intersection of the virtual tangents is determined on the X-ray images, and a triangle is determined. Three corners of the triangle are the point of intersection, and a first point on the first section and a second point on the second section on the X-ray images. The area of the triangle is determined, and the suitable angulation or inclination of the recording system is determined by maximizing the area of the triangle by movement of the recording system.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for automatically determining a suitable angulation or inclination of a recording system for a visualization of a guide wire during a navigation of the guide wire through a vascular system of a patient from a vessel in a branch of the vessel, wherein the guide wire has a curvature and a first proximal section on a first side of the curvature and a second distal section having a tip of the guide wire on a second side of the curvature, the method comprising
    recording a sequence of live X-ray images of the guide wire and presenting the live X-ray images on a display unit;
    identifying the guide wire on at least some X-ray images of the sequence of live X-ray images;
    applying a first virtual tangent to the first section and a second virtual tangent to the second section of the guide wire;
    determining a point of intersection of the first virtual tangent and the second virtual tangent;
    determining a triangle, three corners of the triangle being a point of intersection and a first point on the first section and a second point on the second section, respectively;
    determining an area of the triangle; and
    determining a suitable angulation or inclination of the recording system, the determining of the suitable angulation or inclination comprising maximizing the area of the triangle by movement of the recording system.

2. The method of claim 1, wherein determining the suitable angulation or inclination of the recording system comprises first positioning the recording system, such that a central beam forms a perpendicular on the first section, and thereafter, rotating the recording system around the first section, such that the area of the triangle is maximized.

3. The method of claim 1, wherein determining the suitable angulation or inclination of the recording system comprises first positioning the recording system, such that a central beam forms a perpendicular on the second section, and thereafter, rotating the recording system around the second section, such that the area of the triangle is maximized.

4. The method of claim 1, wherein determining the suitable angulation or inclination of the recording system comprises moving the recording system in an orbital motion, such that the area of the triangle is maximized.

5. The method of claim 1, wherein determining the area of the triangle comprises counting corresponding pixels on the sequence of live X-ray images.

6. The method of claim 1, further comprising subsequently adjusting the suitable angulation or inclination.

7. The method of claim 1, wherein the second point is formed by the tip of the guide wire.

8. The method of claim 1, wherein the first point is formed by an internal point of contact of the first virtual tangent with the first section, and the second point is formed by an internal point of contact of the second tangent with the second section.

9. A medical X-ray device for automatic determination of a suitable angulation or inclination of a recording system for a visualization of a guide wire during a navigation of the guide wire through a vascular system of a patient from a vessel into a branch of the vessel, wherein the guide wire has a curvature and a first proximal section on a first side of the curvature and a second distal section having a tip of the guide wire on a second side of the curvature, the medical X-ray device comprising:

a recording system that is movable in a number of angulations with regard to a patient, the recording system comprising an X-ray source and an X-ray detector for recording X-ray images of the patient;

a controller configured to control the medical X-ray device a display unit configured to display the recorded X-ray images;

an image processor configured to:
   process the recorded X-ray images, the process of the recorded X-ray images comprising:
      automatic application of a first virtual tangent to the first section and a second virtual tangent to the second section based on the displayed recorded X-ray images;
      determination of a point of intersection of the first virtual tangent and the second virtual tangent based on the displayed recorded X-ray images;
      determination of a triangle based on the displayed recorded X-ray images, three corners of the triangle being a point of intersection, the tip of the guide wire, and an arbitrarily determined point on the first section, respectively;
      determination of an area of the triangle based on the displayed recorded X-ray images; and
      determination of a suitable angulation or inclination of the recording system, the determination of the suitable angulation or inclination of the recording system comprising maximization of the area of the triangle by movement of the recording system.

\* \* \* \* \*